US011523929B2

(12) United States Patent
Coppens

(10) Patent No.: US 11,523,929 B2
(45) Date of Patent: Dec. 13, 2022

(54) ACCESSORY DEVICE, A PATIENT IMMOBILIZATION SYSTEM, AND A METHOD OF FORMING A PATIENT IMMOBILIZATION SYSTEM

(71) Applicant: QFIX SYSTEMS, LLC, Avondale, PA (US)

(72) Inventor: Daniel D. Coppens, Avondale, PA (US)

(73) Assignee: QFIX SYSTEMS, LLC, Avondale, PA (US)

( * ) Notice: Subject to any disclaimer, the term of this patent is extended or adjusted under 35 U.S.C. 154(b) by 678 days.

(21) Appl. No.: 15/602,372

(22) Filed: May 23, 2017

(65) Prior Publication Data

US 2017/0333243 A1    Nov. 23, 2017

Related U.S. Application Data

(60) Provisional application No. 62/340,147, filed on May 23, 2016.

(51) Int. Cl.
*A61F 5/37* (2006.01)
*A63B 71/08* (2006.01)
(Continued)

(52) U.S. Cl.
CPC .............. *A61F 5/3707* (2013.01); *A61C 5/90* (2017.02); *A61F 5/3776* (2013.01); *A61N 5/10* (2013.01);
(Continued)

(58) Field of Classification Search
CPC .... A61F 5/56; A61F 5/556; A61F 5/37; A61F 5/3707; A61F 5/3776; A61F 5/0104;
(Continued)

(56) References Cited

U.S. PATENT DOCUMENTS 3,602,913 A    9/1971   Neese
5,531,229 A    7/1996   Dean et al.
(Continued)

FOREIGN PATENT DOCUMENTS

CN    1684636 A     10/2005
FR    2919171 A1    1/2009
(Continued)

OTHER PUBLICATIONS

Lock definition, Merriam Webster Dictionary, definition 3a, https://www.merriam-webster.com/dictionary/lock (Year: 2020).*

(Continued)

*Primary Examiner* — Ophelia A Hawthorne
(74) *Attorney, Agent, or Firm* — RatnerPrestia

(57) ABSTRACT

An accessory device and an immobilization system including the device are provided for positioning at least a portion of a patient's body relative to an immobilization device including a low temperature thermoplastic sheet. The accessory device may include a patient fixation portion and a lock portion. The patient fixation portion is attached to or inserted in the patient during use. The lock portion may extend distally from the patient fixation portion generally along a lock portion axis. The lock portion includes a shape, surface feature, or configuration, such that the low temperature thermoplastic sheet may be conformed to the outer surface of the lock portion of the accessory device, such that unintended separation of the accessory device from the low temperature thermoplastic sheet is prevented. Methods of forming the accessory device and immobilization system are also provided.

25 Claims, 24 Drawing Sheets

(51) Int. Cl.
A61C 5/90 (2017.01)
A61N 5/10 (2006.01)

(52) U.S. Cl.
CPC .... *A63B 71/085* (2013.01); *A61N 2005/1097* (2013.01)

(58) Field of Classification Search
CPC .. A61F 9/02; A61F 9/026; A61F 9/029; A61F 5/566; A61C 5/90; A43B 71/085; A63B 2071/086; A63B 2071/088; A61B 6/042; A61B 6/0421; A61B 6/501; A61B 90/14; A61B 90/16; A61B 90/18; A61N 2005/1097
See application file for complete search history.

(56) References Cited

U.S. PATENT DOCUMENTS

| | | | |
|---|---|---|---|
| 5,538,014 | A | 7/1996 | Wilson et al. |
| 5,865,196 | A | 2/1999 | Foote |
| 6,634,884 | B2 | 10/2003 | Phillips |
| 6,945,251 | B2 | 9/2005 | Woodburn, III |
| 7,290,548 | B2 | 11/2007 | Ungemach et al. |
| 7,461,657 | B2 | 12/2008 | Woodburn |
| 8,419,426 | B2 | 4/2013 | Paris et al. |
| 8,667,970 | B2 * | 3/2014 | Podmore ............ A61M 1/0023 128/848 |
| 9,414,896 | B2 | 8/2016 | Giffey et al. |
| 2002/0108616 | A1 | 8/2002 | Woodburn, III |
| 2003/0082496 | A1 | 5/2003 | Fischer et al. |
| 2006/0005839 | A1 * | 1/2006 | Woodburn ........... A61B 6/0421 128/206.29 |
| 2010/0291504 | A1 | 11/2010 | Paris et al. |
| 2011/0240040 | A1 | 10/2011 | Westbrook et al. |
| 2012/0012120 | A1 | 1/2012 | Giffey et al. |
| 2014/0261430 | A1 * | 9/2014 | Davis .................... A61M 16/06 128/205.25 |
| 2016/0095739 | A1 | 4/2016 | Coppens et al. |

FOREIGN PATENT DOCUMENTS

| | | | | |
|---|---|---|---|---|
| WO | 9733541 | A1 | 9/1997 | |
| WO | 2004032781 | A1 | 4/2004 | |
| WO | WO-2014193938 | A1 * | 12/2014 | ............... A61C 5/90 |

OTHER PUBLICATIONS

European Communication for European Application No. 14734999.7, dated Dec. 11, 2018, 5 pages.
Non Final Office Action for U.S. Appl. No. 14/894,030, dated Apr. 11, 2019, 37 pages.
Final Office Action for U.S. Appl. No. 14/894,030 dated Sep. 25, 2019, 15 pages.
Chinese Office Action for Chinese Application No. 201480042655.3, dated May 21, 2018, with English translation, 23 pages.
TruGuard, Custom Tongue and Jaw Positioner, Bionix Radiation Therapy, 2018, 2 pages.
Chinese Office Action for Chinese Application No. 201480042655.3, dated Jun. 30, 2017, including English translation, 11 pages.
International Preliminary Report on Patentability and Written Opinion for International Application No. PCT/US2014/039764 dated Dec. 1, 2015, 7 pages.
International Search Report for International Application No. PCT/US2014/039764 dated Aug. 28, 2014, 4 pages.
Extended European Search Report for European Appiication No. 20 184 556.7, dated Oct. 29, 2020, 8 pages.
Non Final Office Action for U.S. Appl. No. 14/894,030, dated Aug. 31, 2020, 21 pages.
Final Office Action for U.S. Appl. No. 14/894,030, dated May 11, 2021, 23 pages.
"Opening", yourdictionary.com, https://www.yourdictionary.com/opening, Retrieved from the internet on May 6, 2021, 7 pages.
The Free Dictionary by Farlex, "thermoplastic," downloaded at https://www.thefreedictionary.com/Thermoplastics, 2021, 1 page.
Non Final Office Action for U.S. Appl. No. 14/894,030, dated Nov. 9, 2021, 27 pages.
Bionix, 510K TruGuard Custom Tongue and Jaw Positioner (https://www.accessdata.fda.gov/cdrh_docs/pdf15/K153270.pdf),10 pgs, Mar. 8, 2016, U.S. Dept. of Health & Human Services, Silver Spring, MD.†
Civco 2005-2006 Sourcebook, Medtec Radiation Oncology Accessories, 3 pgs, 2005-2006.†
Civco Medical Solutions Patient Positioning, Fixation and Localization, 3 pgs, 2006.†
Radiation Oncology Civco 2010 Sourcebook, pp. 3, 2010.†
Radiation Oncology Civco 2011 Sourcebook, pp. 3, 2011.†

\* cited by examiner
† cited by third party

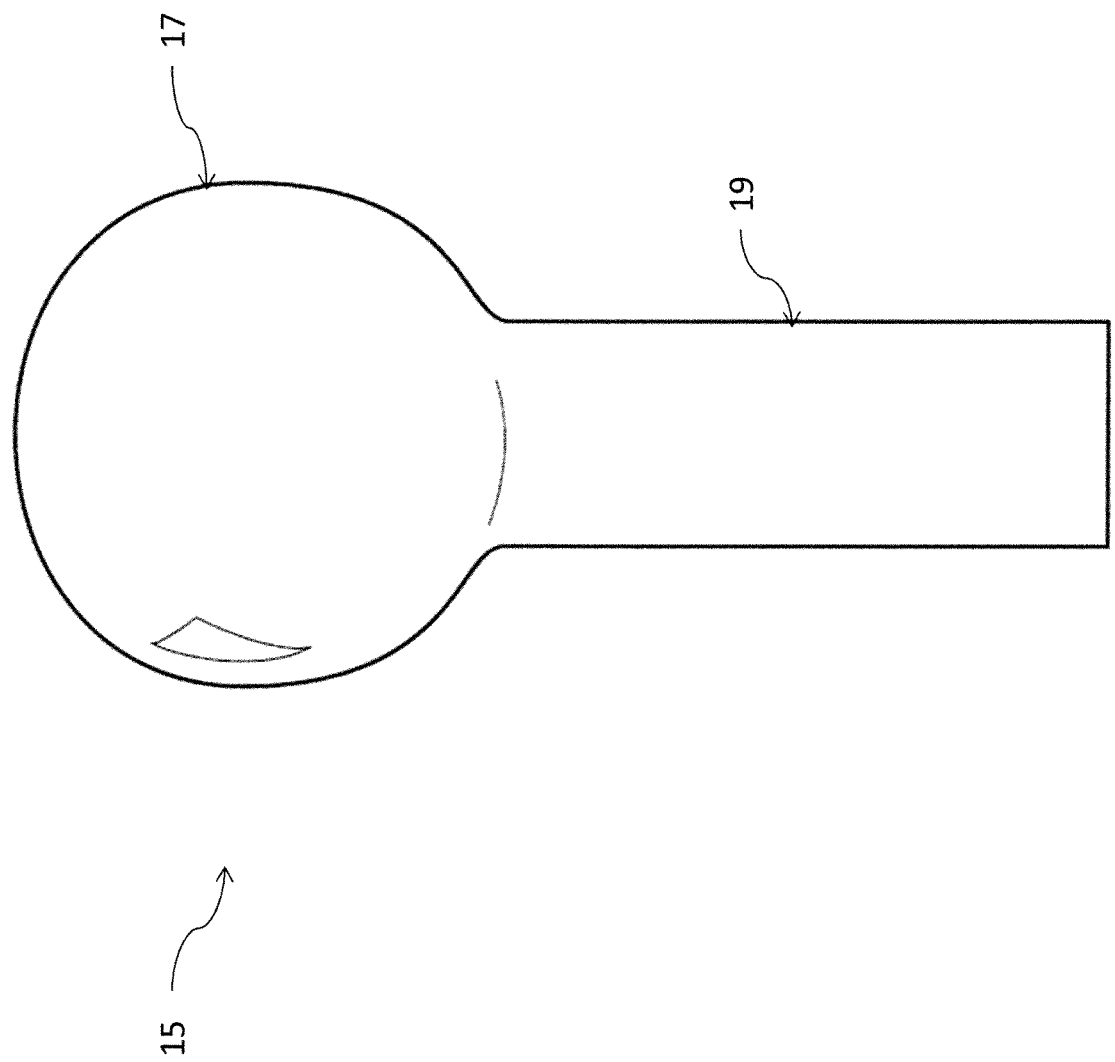

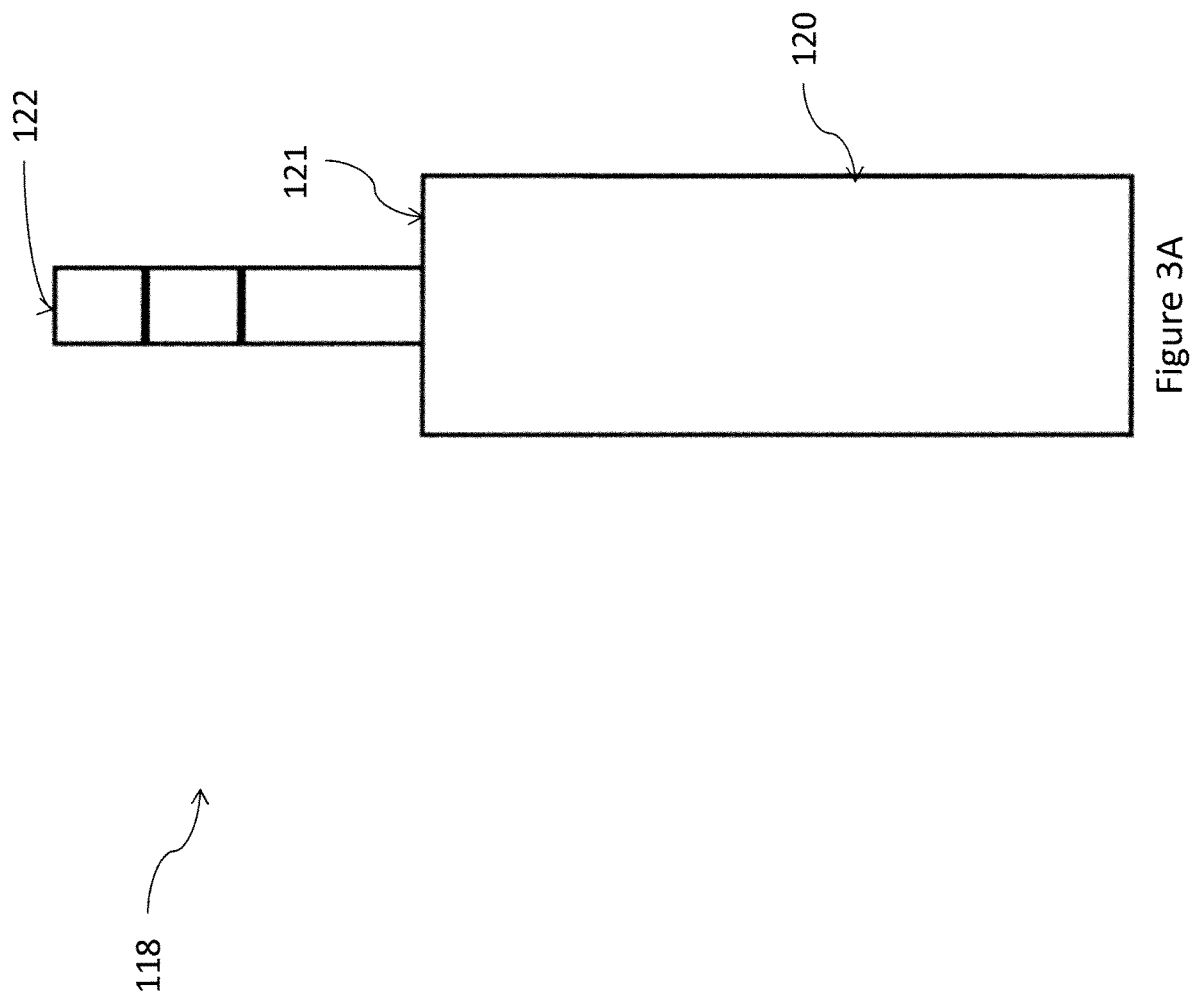

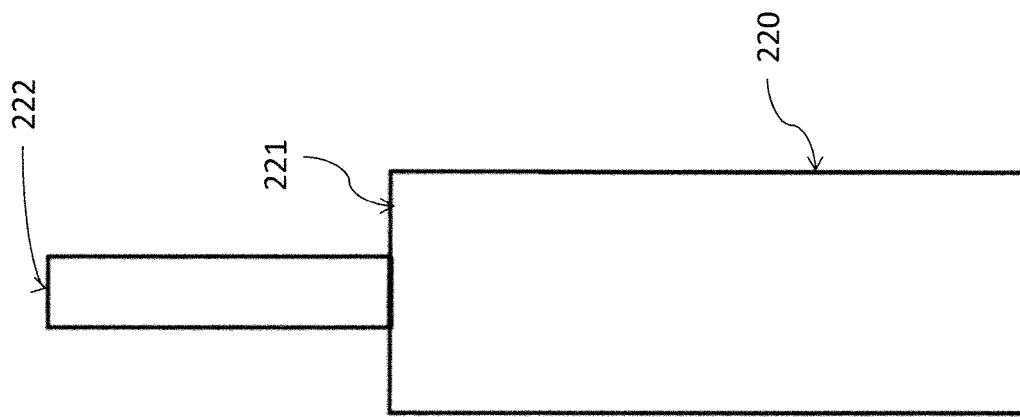

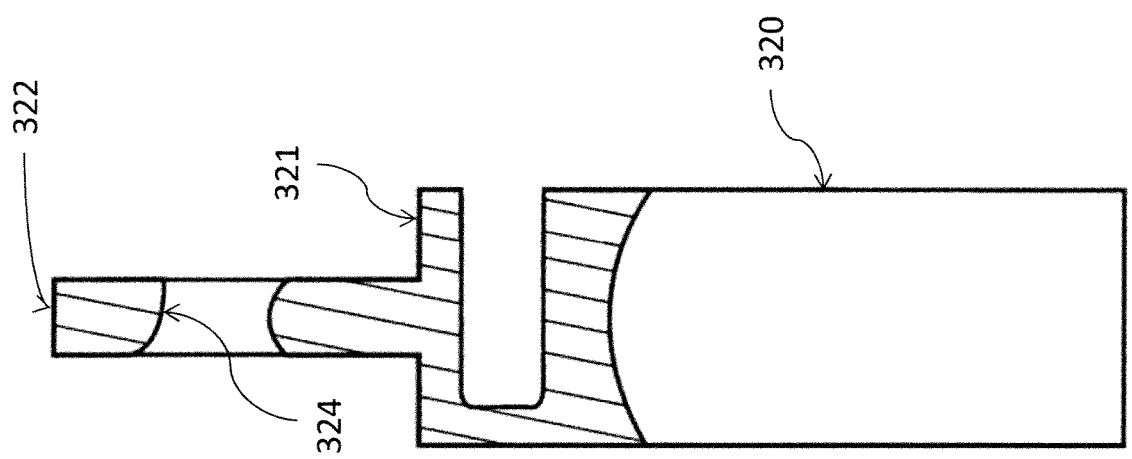

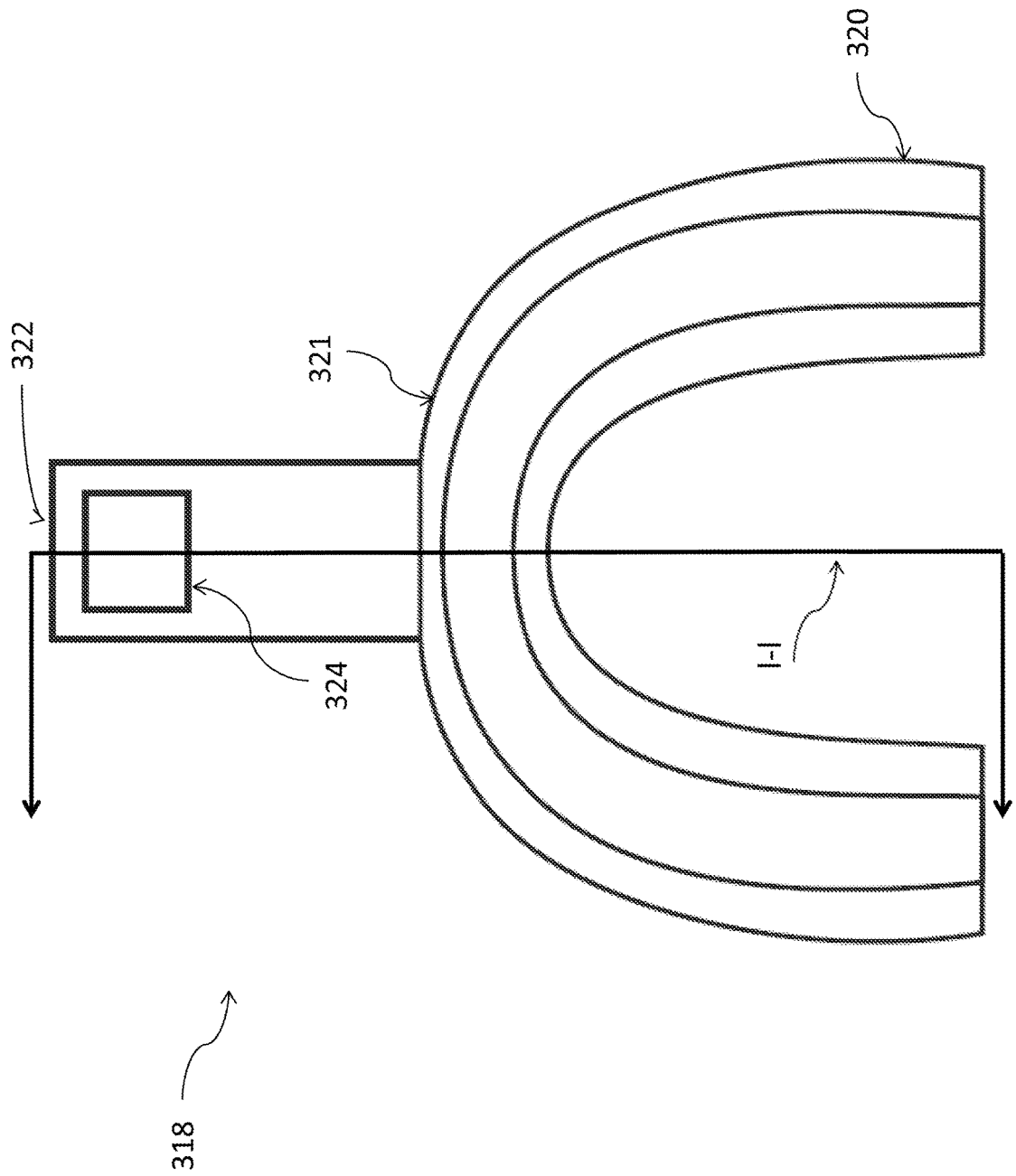

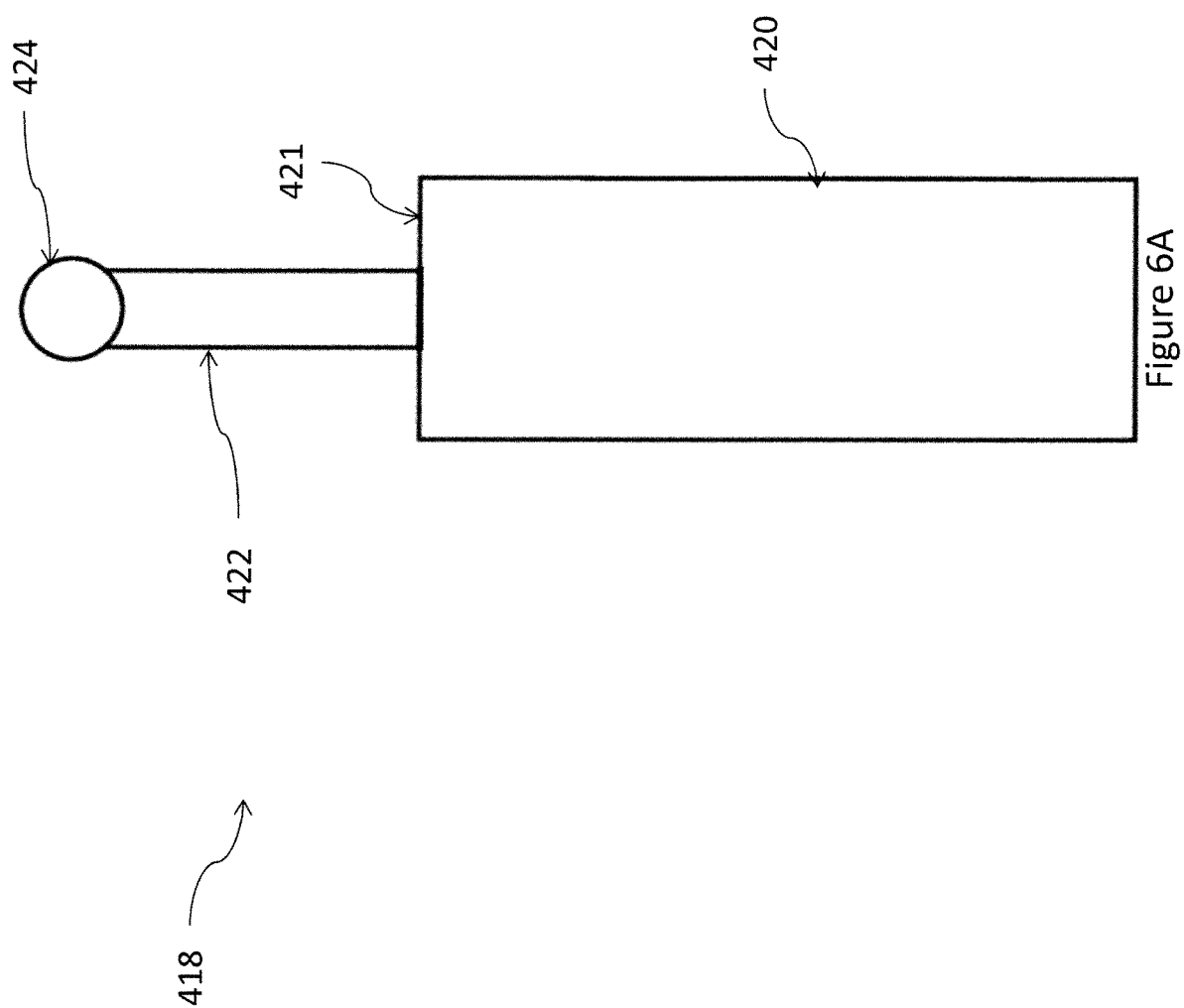

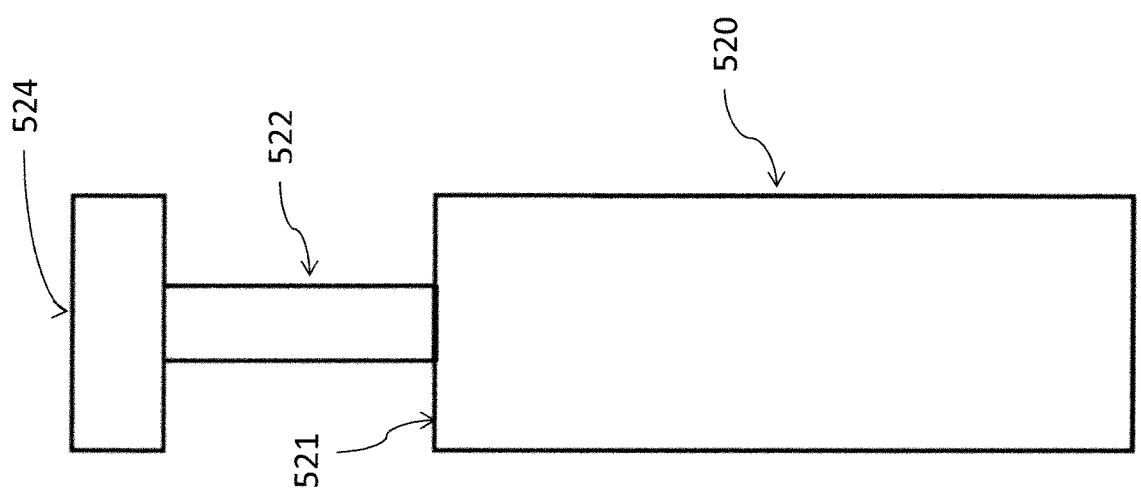
Figure 7A

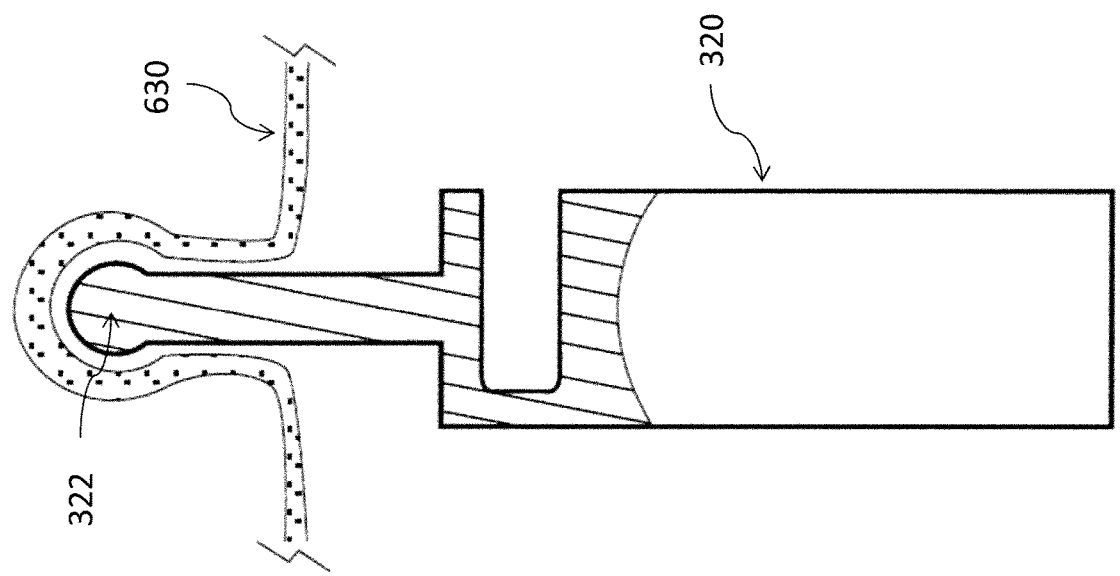

ACCESSORY DEVICE, A PATIENT IMMOBILIZATION SYSTEM, AND A METHOD OF FORMING A PATIENT IMMOBILIZATION SYSTEM

CROSS REFERENCE TO RELATED APPLICATIONS

This application claims priority to and benefit of U.S. Provisional Patent Application No. 62/340,147, filed May 23, 2016, the entire disclosure of which is incorporated herein by reference.

FIELD OF THE INVENTION

This invention relates to an accessory device for positioning a patient, an immobilization system, and a method of forming an immobilization system for immobilizing at least a portion of a patient's body.

BACKGROUND OF THE INVENTION

In radiotherapy treatment of cancer, low temperature (LT) thermoplastic immobilization preforms in the form of sheets are often formed over a patient's body to limit patient motion during imaging and/or treatment. Examples of LT thermoplastic materials include Aquaplast and Fibreplast (manufactured by Qfix Systems, LLC of Avondale, Pa.).

Over the years, various advances have been made to improve immobilization systems. For example, US-2016-0095739-A1 discloses a bite plate that is used in conjunction with LT thermoplastic for immobilizing a patient's head. Nevertheless, there remains a need for further improvements in immobilization systems.

SUMMARY OF THE INVENTION

According to one aspect of the present invention, an accessory device is configured to position a patient relative to an immobilization device including a low temperature thermoplastic sheet. The accessory device may include a patient fixation portion configured for fixation on or insertion into the patient during use and a lock portion extending distally from the patient fixation portion generally along a lock portion axis. The accessory device may be configured to be engaged by a proximal surface of the low temperature thermoplastic sheet by forming the proximal surface of the low temperature thermoplastic sheet around the lock portion of the accessory device, such that the proximal surface of the low temperature thermoplastic sheet conforms to the lock portion and the engagement prevents unintended separation of the accessory device from the low temperature thermoplastic sheet during use.

According to another aspect of the present invention, the accessory device may be combined with a low temperature thermoplastic sheet to provide an immobilization system configured to immobilize a patient.

According to yet another aspect of the present invention, a method of forming an immobilization system configured to immobilize at least a portion of the patient's body is provided. The method comprises the steps of attaching or inserting a patient fixation portion of an accessory device on or in the patient, positioning a proximal surface of a low temperature thermoplastic sheet of an immobilization device adjacent a lock portion of an accessory device extending distally from the patient fixation portion, forming the low temperature thermoplastic sheet of the immobilization device about the portion of the patient's body, and forming the proximal surface of the low temperature thermoplastic sheet around the lock portion of the accessory device, such that unintended separation of the accessory device from the low temperature thermoplastic sheet is prevented.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 1 is a general schematic of an accessory device according to an aspect of the present invention;

FIG. 3A is a side view of a second embodiment an accessory device according to an aspect of the present invention;

FIG. 4A is a side view of a third embodiment of an accessory device according to an aspect of the present invention;

FIG. 5A is a side view of a cross-section of a fourth embodiment of the present invention along axis I-I in FIG. 5B;

FIG. 5B is a top plan view of the fourth embodiment of an accessory device according to an aspect of the present invention;

FIG. 6A is a side view of a fifth embodiment of an accessory device according to an aspect of the present invention;

FIG. 7A is a side view of a sixth embodiment of an accessory device according to an aspect of the present invention;

FIG. 11 is a side view of the cross section of the embodiment of FIG. 6A on which a portion of an LT thermoplastic material has been crimped;

DETAILED DESCRIPTION OF THE INVENTION

Figure 2A:
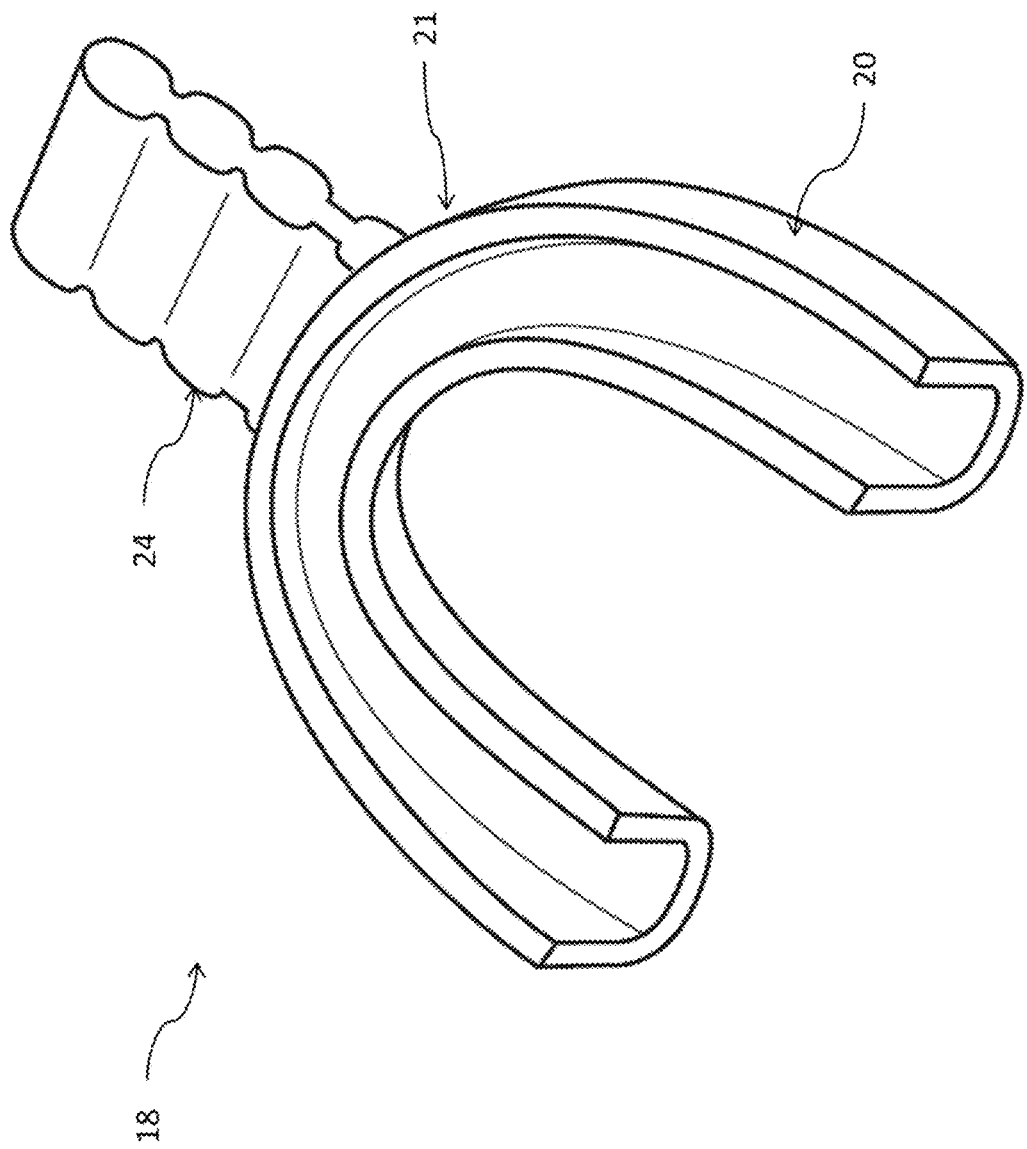
FIG. 2A is a perspective view of a first embodiment of an accessory device according to an aspect of the present invention.

Although the invention is illustrated and described herein with reference to specific embodiments, the invention is not intended to be limited to the details shown. Rather, various modifications may be made in the details within the scope and range of equivalents of the claims and without departing from the invention.

Bite plates, ear inserts, and other accessories may be incorporated into immobilization systems to improve the quality of immobilization and repeatability from simulation through each treatment fraction, such as the apparatus disclosed in U.S. Pat. No. 6,945,251. Such accessories can be either attached through multi-component mechanical fasteners or through secondary adhesive application used to bond the accessory to a LT thermoplastic. In some instances, however, such systems encounter difficulty associated with attaching the accessories to the surface of the LT thermoplastics because the surface is typically a low friction, anti-stick surface, so that the material does not stick to the patient or to itself.

In US-2016-0095739-A1, a bite plate is inserted from the outside of the LT thermoplastic. While this solution represents an improvement, the size of the overall attached accessory can be limited and detailed contouring of anatomical features, such as the ear, may be difficult in some instances.

The accessory device according to the various embodiments of this invention comprises a piece, or lock portion, that is mechanically fastened to an LT thermoplastic immobilizer through a direct mechanical fastening created by the LT thermoplastic immobilizer. The accessory device includes a portion that is applied to or inserted in the patient. The accessory device also includes a locking feature that is configured to allow a portion of the LT thermoplastic to be wrapped around the locking feature. The accessory device may be of single-piece design to provide a less complex system that is easier for the clinician to use and reduces the number of parts that can be lost or misplaced.

The accessory device includes a patient fixation portion designed for a variety of applications familiar to one skilled in the art. These include, but are not limited to, a mouthpiece, ear insert, nasion fixator, tongue block, etc.

The present invention also includes methods of immobilizing a patient by attaching an accessory device to a thermoplastic preform. In one embodiment, the accessory device comprises a patient fixation portion and a locking feature. The locking feature can be of several forms as described later herein. According to one method of the present invention, the accessory device may include a patient fixation portion in the form of a mouthpiece placed in the patient's mouth, and the patient is allowed to bite down on the mouthpiece. The locking feature may be configured such that it extends out of the patient's mouth.

Pre-heated LT thermoplastic sheet is then formed over the locking feature and the patient and attached to a base plate to keep the preform in place as it cools. Base plates on other immobilization hardware (such as those incorporated in the Portrait and Encompass systems manufactured by Qfix Systems, LLC of Avondale, Pa.) are optionally used.

While the LT thermoplastic material is still soft, a portion of the material is formed or wrapped around the locking feature of the accessory device. Once cooled and hardened, the LT thermoplastic material will be secured as a result of pinching, clamping, or clutching forces of the material about the locking feature. It is preferred that a close mechanical contact is provided between the LT thermoplastic material and the locking feature to provide a rigid mechanical interlock. This pinching, crimping, or compressing can be accomplished manually by hand or with a tool, such as a clothes pin, a hemostat, pliers, or any other such tool as would be known to one skilled in the art.

The patient fixation portion of the accessory device may be made of a rigid, semi-rigid, or flexible material. In addition, the patient fixation portion may be made from a reformable material, such as Aquaplast or Fibreplast, that is able to conform or assume the shape of a patient's mouth to promote comfort as well as the ability to repeatedly remove and replace the mask in the same position. The locking feature of the accessory device may comprise either the same or different material than the patient fixation portion. For example, in one embodiment, the locking feature may be made of a rigid material, or a material that is more rigid than the patient fixation portion, so that the shape of the locking feature is not malleable or susceptible to changing shape during fixation to the LT thermoplastic material. Alternatively, in another embodiment, the locking feature may be as malleable or more malleable than the patient fixation portion of the fixation device, so that the locking feature may be molded during fixation to the LT thermoplastic material. The inclusion of channels and port to apply a vacuum may be included in the patient fixation portion in yet another embodiment of the invention described in greater detail below.

The locking feature of the accessory device according to the various embodiments of the present invention may be configured in a variety of geometries. It is preferred that the geometry allows preheated/softened LT thermoplastic material to be wrapped around the locking feature so that the accessory device and LT thermoplastic material are fixedly coupled to each other when the LT thermoplastic material cools and/or hardens. It is particularly preferred that the connection between the locking feature and the LT thermoplastic material firmly locks all six degrees of freedom of the accessory with respect to the LT thermoplastic material. For example, the geometry of the locking feature may be such that the shape minimizes any air gaps between the locking feature and the hardened LT thermoplastic material. The shape and size of the locking feature may be selected based on the desired connection between the accessory device and the LT thermoplastic material and the specific application for the patient.

Referring now to the figures, various embodiments of an accessory device 18 according to the present invention are illustrated. In FIG. 1, a general schematic illustrating the relative positions of the patient fixation portion 17 and a lock feature 19 of an accessory device 15 is provided. The patient fixation portion 17 is represented as a sphere; however, the patient fixation portion 17 is preferably configured to conform to patient specific anatomy depending on the location that the patient fixation portion will be applied or inserted. For example, in the remaining figures, various embodiments of the present invention are illustrated in which the patient fixation portion is intended for oral insertion; however, as noted above, the patient fixation portion of the accessory device may be configured for use as an ear insert, nasion fixator, or tongue block, for example.

Figure 2B:
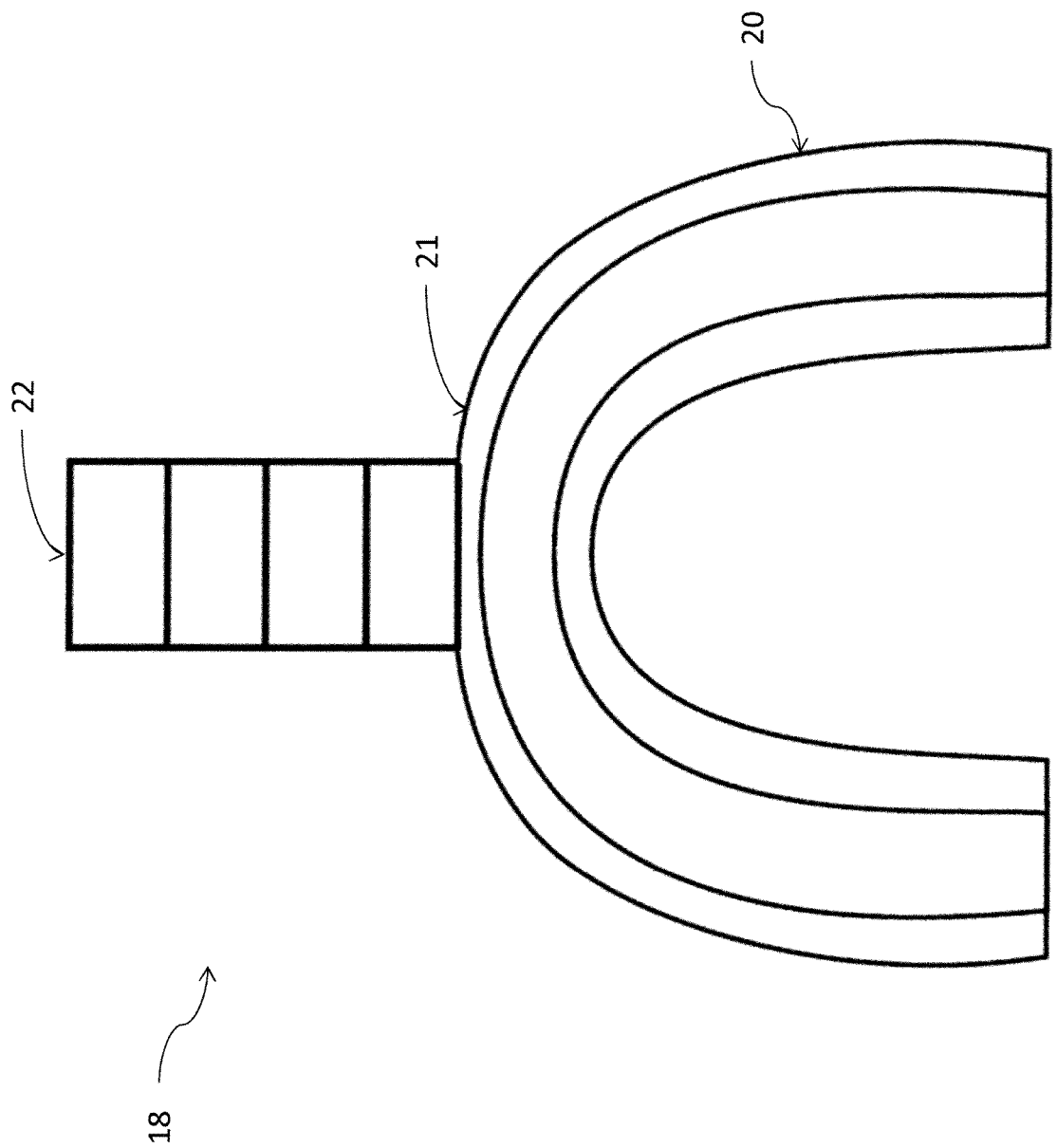
FIG. 2B is a top plan view of the embodiment of FIG. 2A.
Figure 3B:
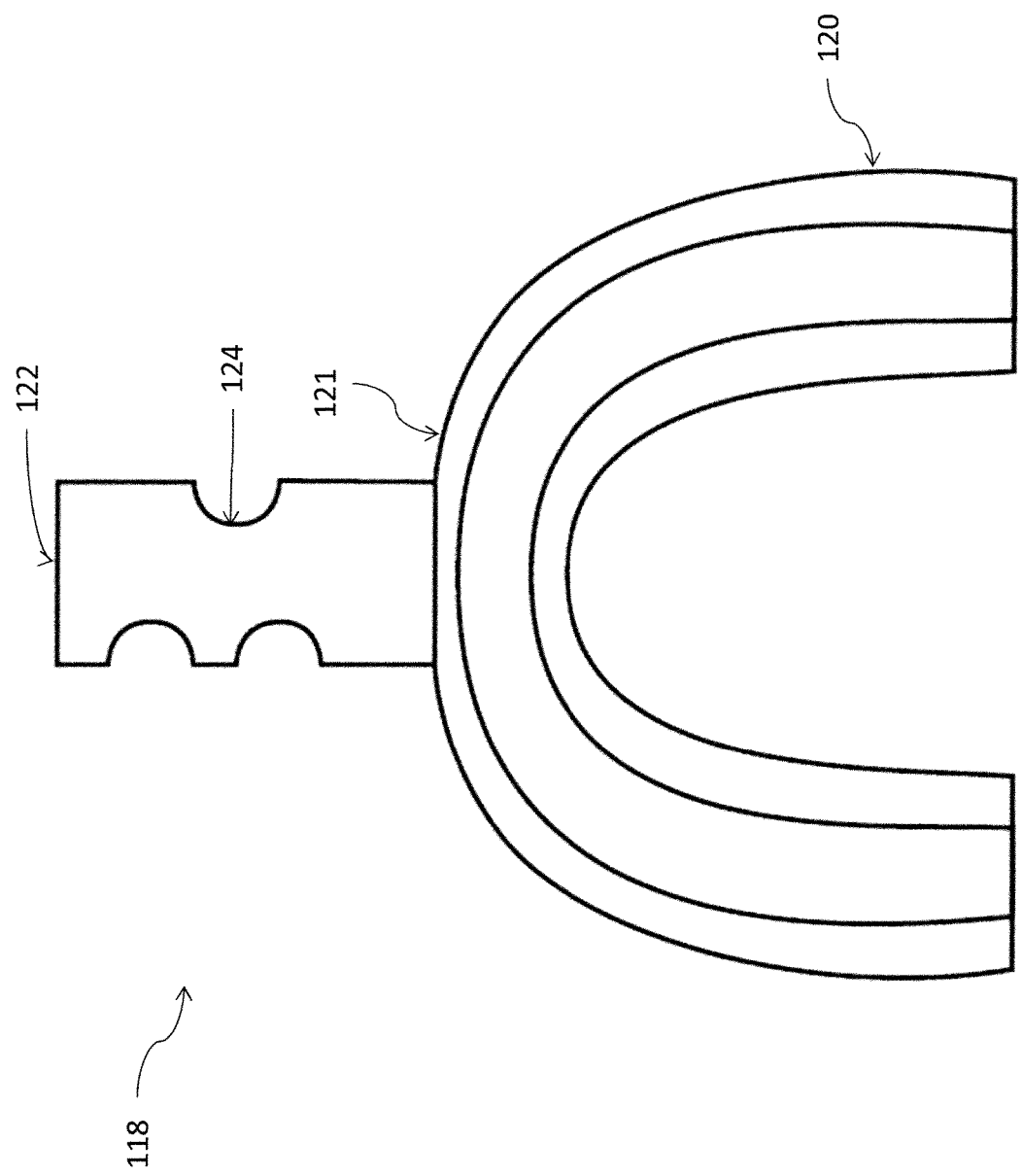
FIG. 3B is a top plan view of the embodiment of FIG. 3A.
Figure 4B:
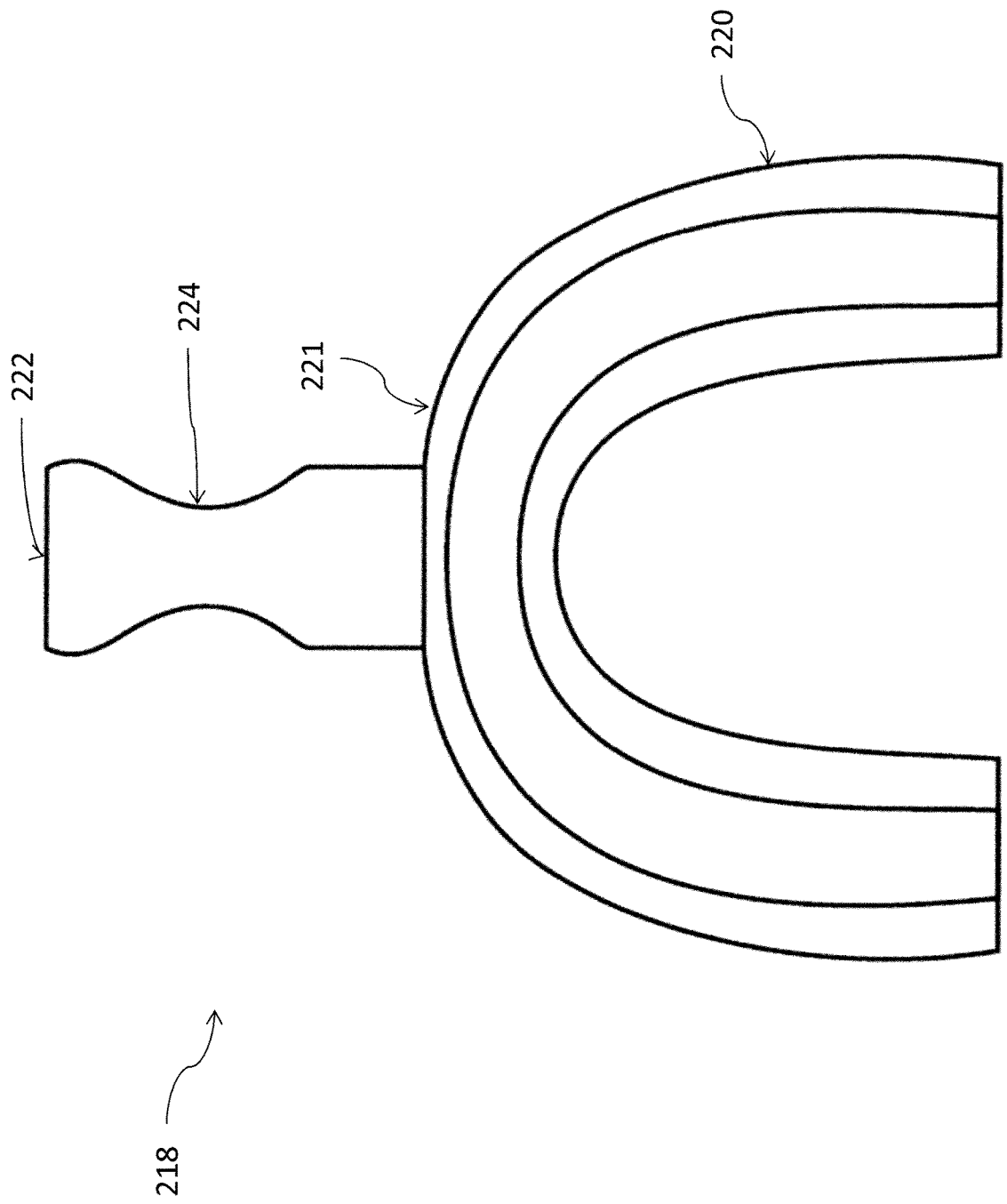
FIG. 4B is a top plan view of the embodiment of FIG. 4A.
Figure 6B:
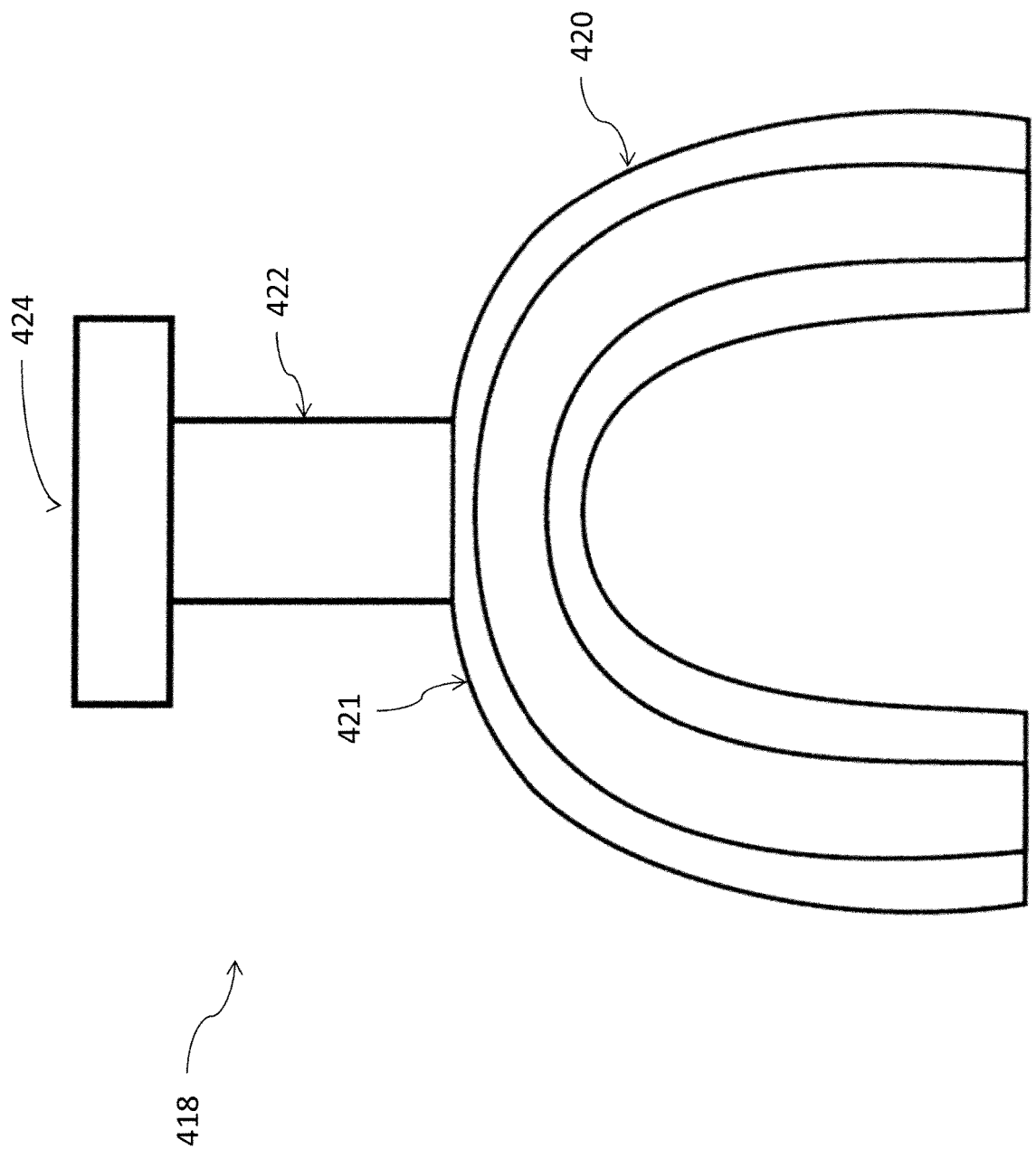
FIG. 6B is a top plan view of the embodiment of FIG. 6A.

In FIGS. 2A and 2B, an accessory device 18 according to a first embodiment of the present invention is provided. The accessory device 18 is of a single piece design and includes a patient fixation portion 20 in the form of a mouthpiece and a locking feature 22. The patient fixation portion 20 is U-shaped to provide an area that is substantially proportional to the area of a patient's bite. Projecting from a front surface 21 of the patient fixation 20 is a locking feature 22. The locking feature 22 of the first embodiment includes a substantially uniform width, but a variable height because the locking feature 22 includes a plurality of ridges 24. The undulations on the top and bottom surface of the locking feature 22 provide an area for forming an interlocking surface with an LT thermoplastic material, thereby preventing accessory device 18 from being withdrawn from the LT thermoplastic material after a softened LT thermoplastic material has been crimped onto at least one ridge 24 and along the sides of the locking feature 22 while the material is allowed to harden.

In FIGS. 3A to 8B, several embodiments of the present invention are illustrated. The accessory devices (118, 218, 318, 418, 518, 618) according to the additional embodiments are also a single piece design and include a patient fixation portion (120, 220, 320, 420, 520, 620) that is substantially similar to the first embodiment. The additional embodiments also include locking features (122, 222, 322, 422, 522, 622) that project from a front surface (121, 221, 321, 421, 521, 621) of the patient fixation portion (120, 220, 320, 420, 520, 620); however, the shape of the various locking features differ.

For examples in FIGS. 3A, 3B, 4A, and 4B, the locking feature 122, 222 includes a plurality of notches 124, 224 of different sizes and shapes located at different locations along the sides of the locking feature 122, 222. Alternatively, one or more openings, such as a hole, bore, or aperture, may be provided within the locking feature, such as the square-shaped hole 324 in the locking feature 322 in the embodiment of FIGS. 5A and 5B. The shape, size, and thickness of the hole should be selected to allow for LT thermoplastic material to substantially fill the hole when crimped onto the locking feature. Alternatively, the locking feature may be provided with one or more projections. For example, the locking feature may be T-shaped, similar to the embodiments in FIGS. 6A to 6B. Other shapes may include, but are not limited to, Y-shapes, X-shapes, fan shapes, bow-tie shapes, ring shapes, oblong shapes, rhombus (lozenge) shapes, etc. The projections (424) may extend in the transverse direction, the projections (524) may extend in the superior/inferior direction, or at any angle about any axis, as long as the LT thermoplastic material may be crimped around the locking feature and air gaps around the locking feature are minimized, i.e. contact between the LT thermoplastic material and the outer surface of the locking feature is maximized.

Figure 7B:
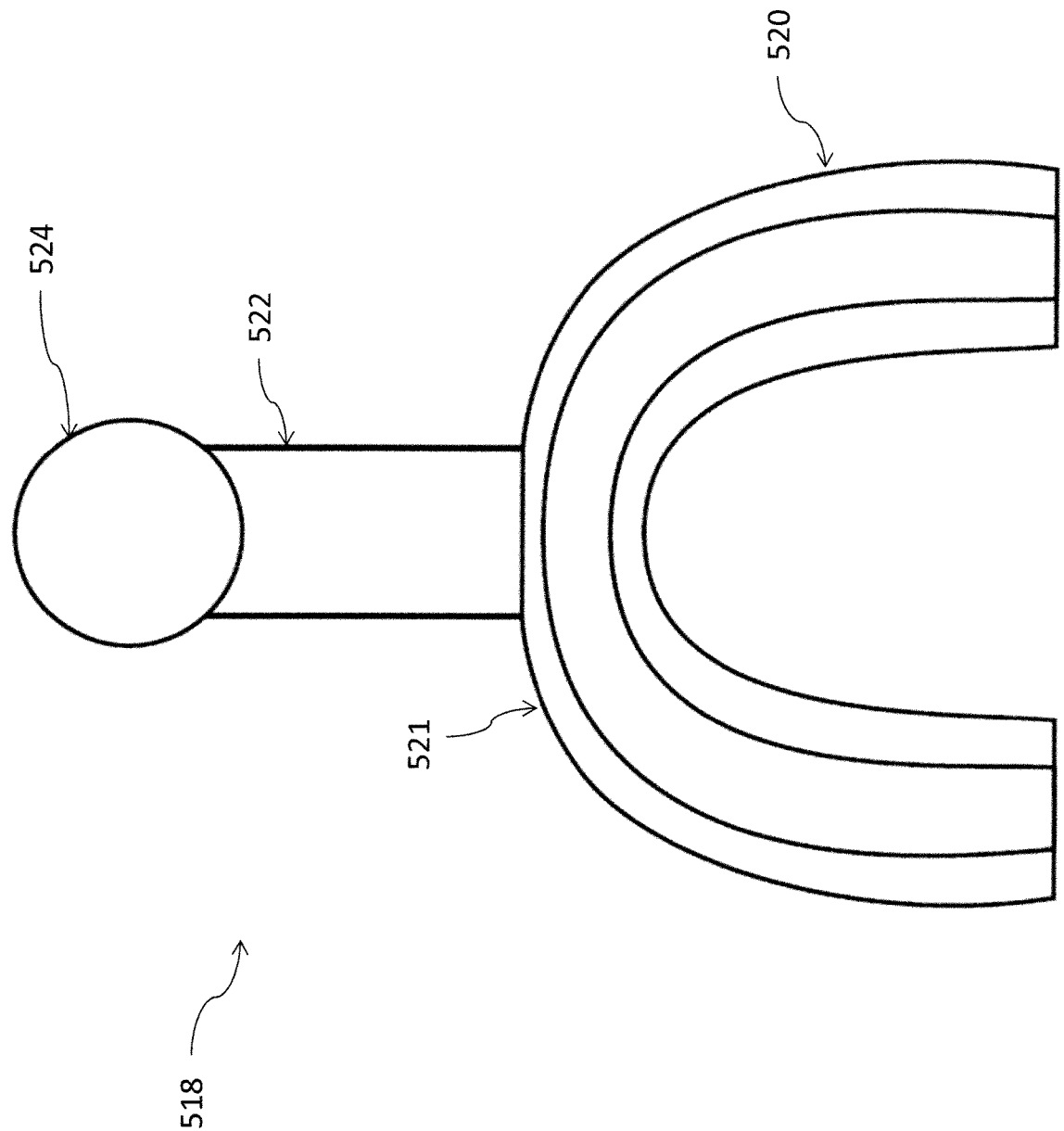
FIG. 7B is a top plan view of the embodiment of FIG. 7A.
Figure 14:
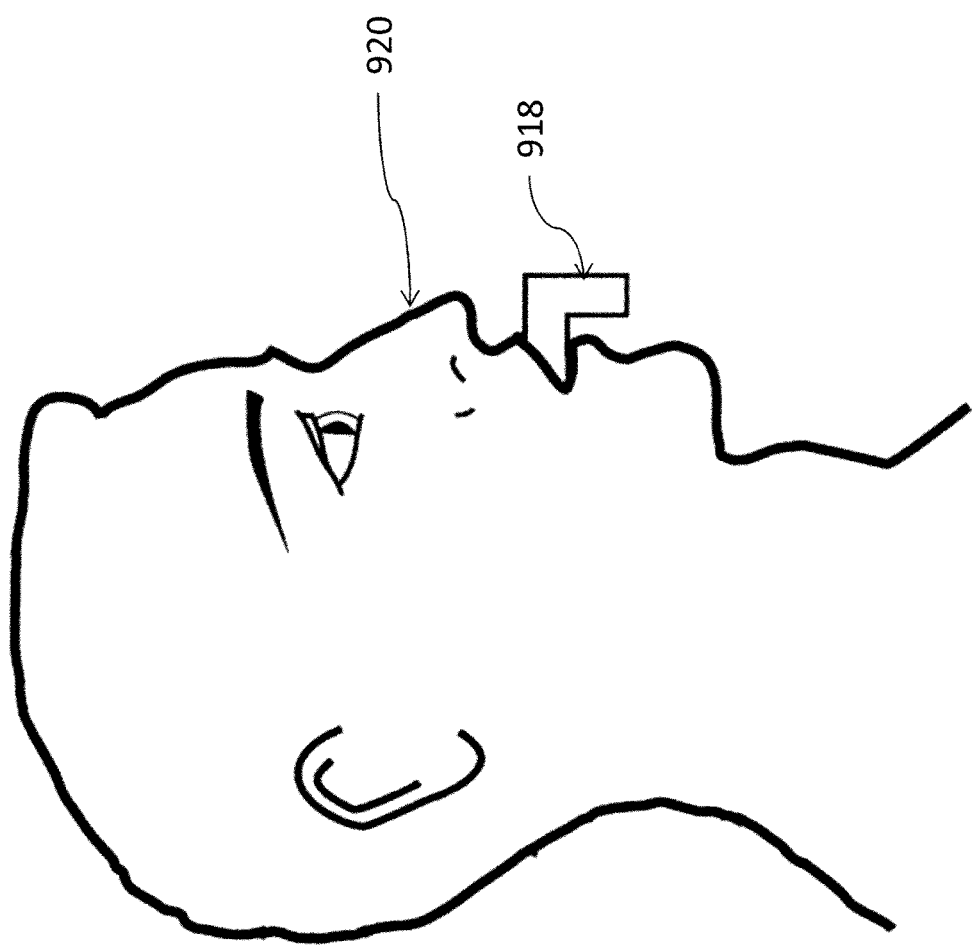
FIG. 14 is a side view of tenth embodiment of an accessory device according to an aspect of the present invention orally inserted in a patient.

The embodiment of FIGS. 7A and 7B having the projections in the superior/inferior direction also provides an additional advantage during imaging and radiotherapy. For example, the projections may serve as reference markers for optical tracking systems, such OSMS and AlignRT from VisionRT, as well as with the Sentinel system from C-Rad. Aligning the locking feature longitudinally (superior to inferior) may keep the locking feature from blocking the main zero degree camera's view of the patient's facial anatomy. At the same time, it may provide lateral cameras with a feature that can potentially be used for tracking. Alternatively, the locking feature may be L-shaped instead of T-shaped, so that the locking feature projects away from the patient's nose 920, such as locking feature 918 in FIG. 14, which may provide better access for optical tracking systems.

Figure 12:
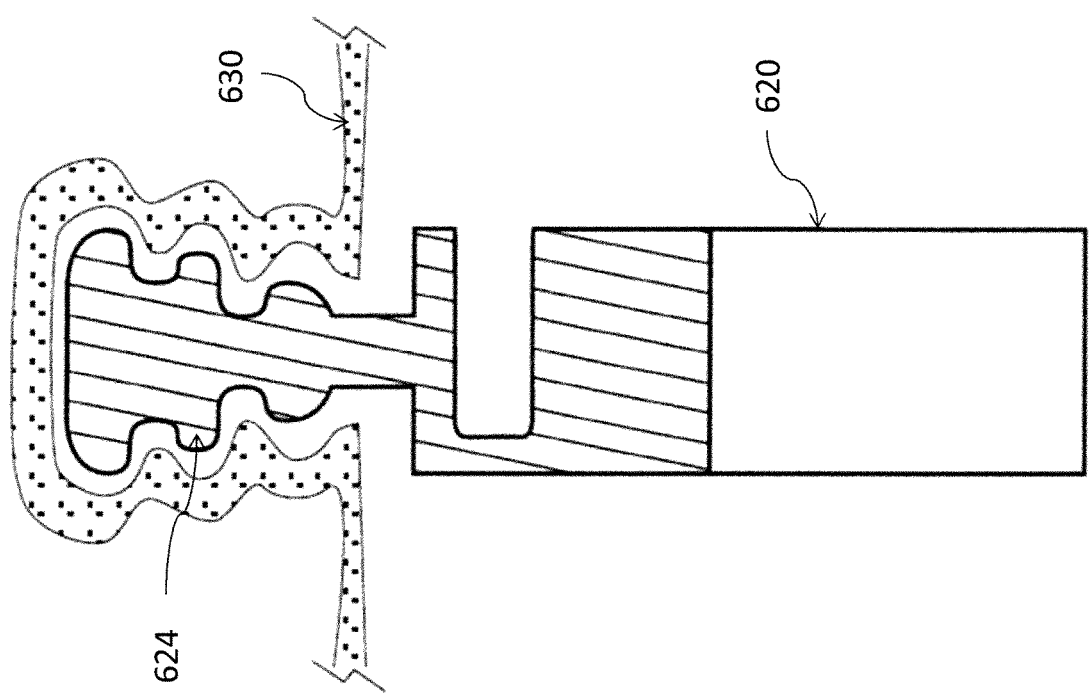
FIG. 12 is a side view of the cross section of the embodiment of FIG. 8A on which a portion of an LT thermoplastic material has been crimped.

As would be understood by one of skill in the art, the location and shape of the various features on the surface of the locking feature may be varied, as long as the locking feature is provided with a surface that will prevent the accessory device from being withdrawn from a hardened LT thermoplastic material when the accessory device is in the installed condition, as illustrated in FIGS. 11 and 12. As shown in FIG. 11, the lock portion 322 does not penetrate the low temperature thermoplastic sheet 630. Also as shown in FIG. 12, the lock portion 624 does not penetrate the low temperature thermoplastic sheet 630.

As illustrated in the figures, the locking feature is shown projecting from the midpoint of the front surface of the patient fixation portion; however, as would also be appreciated by those of skill in the art, one or more locking features may project from various locations on the front surface of the patient fixation portion in different directions. It is preferred that a plurality of locking features extend from the front surface of the mouthpiece at different angles, so that the accessory device is not limited to uses wherein the patient is in the supine position. This may also be achieved with a single locking feature, for example, if the accessory device is of a two-part design in which the locking feature is allowed to slide or rotate relative to the front surface of the mouthpiece.

Figure 8A:
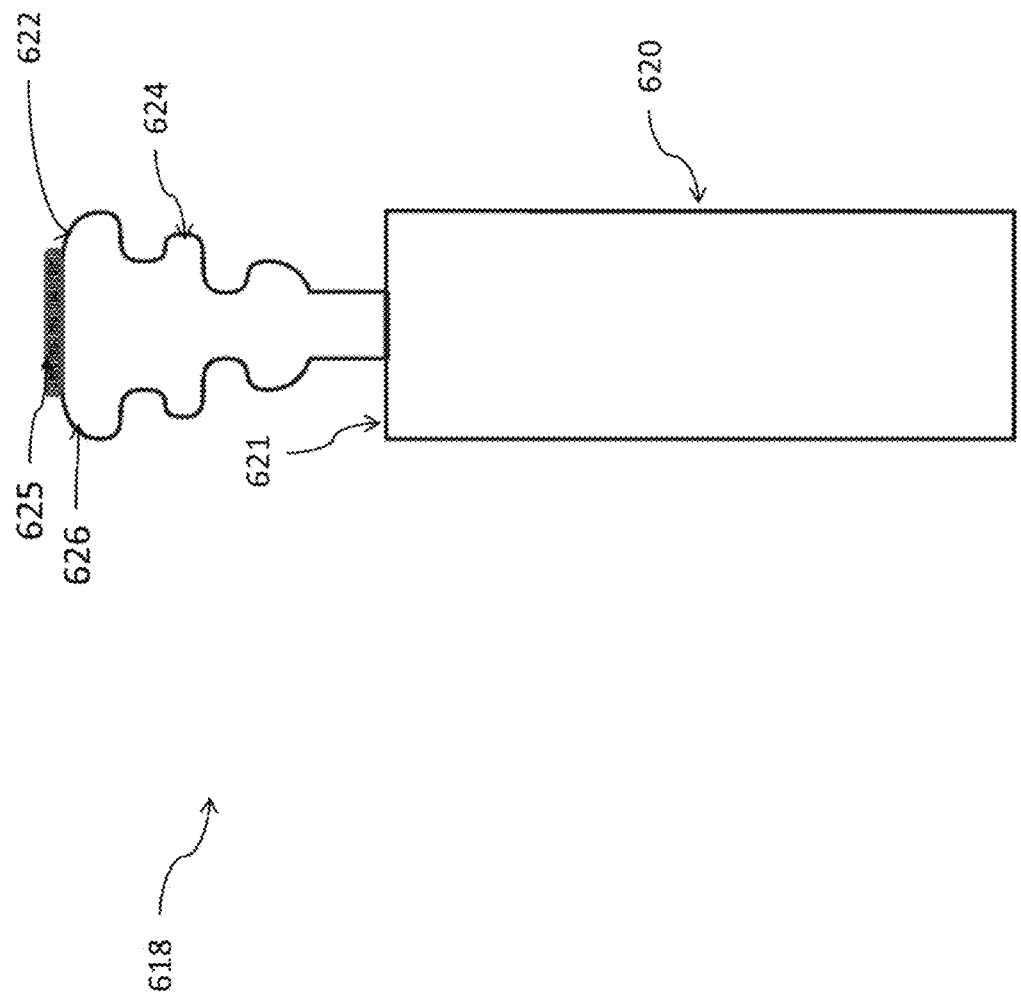
FIG. 8A is a side view of a seventh embodiment of an accessory device according to an aspect of the present invention.
Figure 8B:
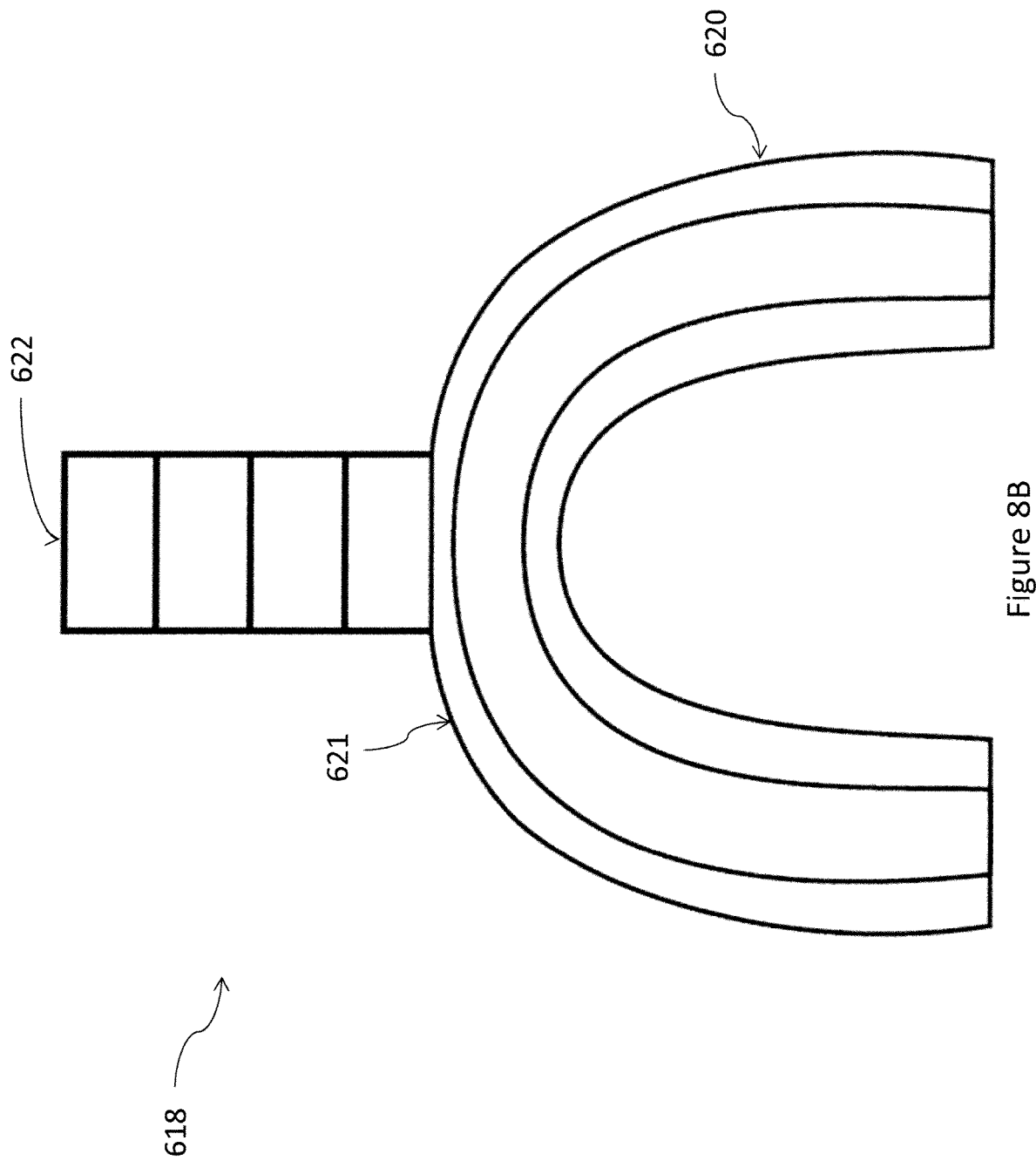
FIG. 8B is a top plan view of the embodiment of FIG. 8A.

Yet another embodiment of a present invention is provided in FIGS. 8A and 8B. Again, the accessory device 618 is essentially the same as the previous embodiments. The accessory device 618 comprises a patient fixation portion in the form of a U-shaped mouthpiece 620 having a front surface 621 from which a locking feature 622 extends. In the embodiment of FIGS. 8A and 8B, the locking feature is in the form of a wedge with ridges, e.g. an "inverted Christmas tree". This configuration (as well as others) can benefit from a forming tool to allow the clinician to form the LT thermoplastic material into all of the folds of the locking feature. This embodiment shows an adhesive coating (625) on a surface (626) of the engaging end portion (624).

Figure 9:
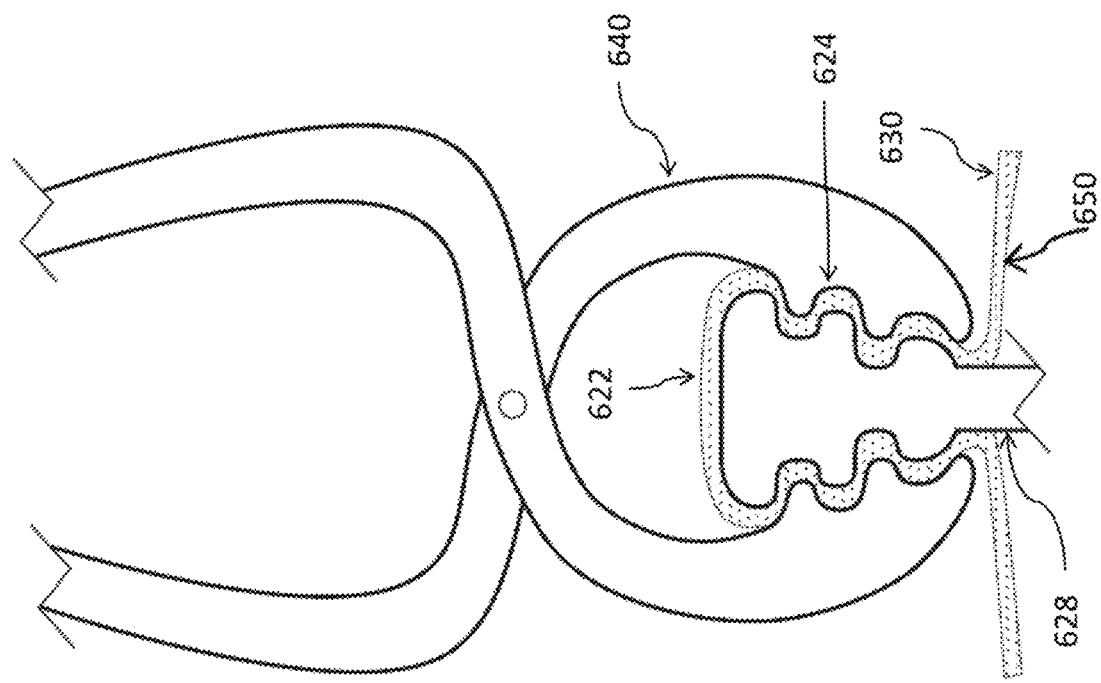
FIG. 9 is a side view of the locking feature of the embodiment of FIG. 8A on which a portion of an LT thermoplastic material has been crimped.

FIG. 9 demonstrates how a tool may be provided to aid in the application of the softened LT thermoplastic material 630 to the locking feature during forming. The tool 640 may be in the form of pliers or similar crimping device, wherein the crimping end of the tool includes a similarly shaped surface to the engaging end portion 624 of the lock portion 622, which extends distally from a bite portion (not shown) generally along a lock portion axis. This maximizes the contact between the inner surface of a portion of the LT thermoplastic material 630 and the engaging end portion 624 of the lock portion 622. To further minimize the potential for air gaps, pressure may be maintained using the tool until the LT thermoplastic material hardens around the lock portion 622. The lock portion 622 may also include a stem portion 628 connecting the lock portion 624 to the bite portion of the accessory device. The stem portion 628 is preferably sufficiently long to prevent the potential of the tool 640 pinching the patient's flesh. The engaging end portion 624 may have a variable cross-sectional area along and orthogonal to the lock portion axis. As would be appreciated by those of skill in the art, the engaging end portion of the lock portion may alternatively have a generally uniform cross section along and orthogonal to the lock portion axis, but provided, for example, with a coiled or twisted configuration to prevent unintended separation of the accessory device from the low temperature thermoplastic sheet in the engaged condition.

The accessory device may be configured to be engaged by a proximal surface 650 of the low temperature thermoplastic sheet 630 by forming the proximal surface 650 of the low temperature thermoplastic sheet around the engaging end portion 624 of the lock portion 622 of the accessory device, such that the proximal surface 650 of the low temperature thermoplastic sheet 630 contacts the reduced cross-sectional area of the engaging end portion 624 and the engagement prevents unintended separation of the accessory device from the low temperature thermoplastic sheet during use. As shown in FIG. 9, in the engaged condition, the lock portion 622 does not penetrate the low temperature thermoplastic sheet 630.

Figure 10A:
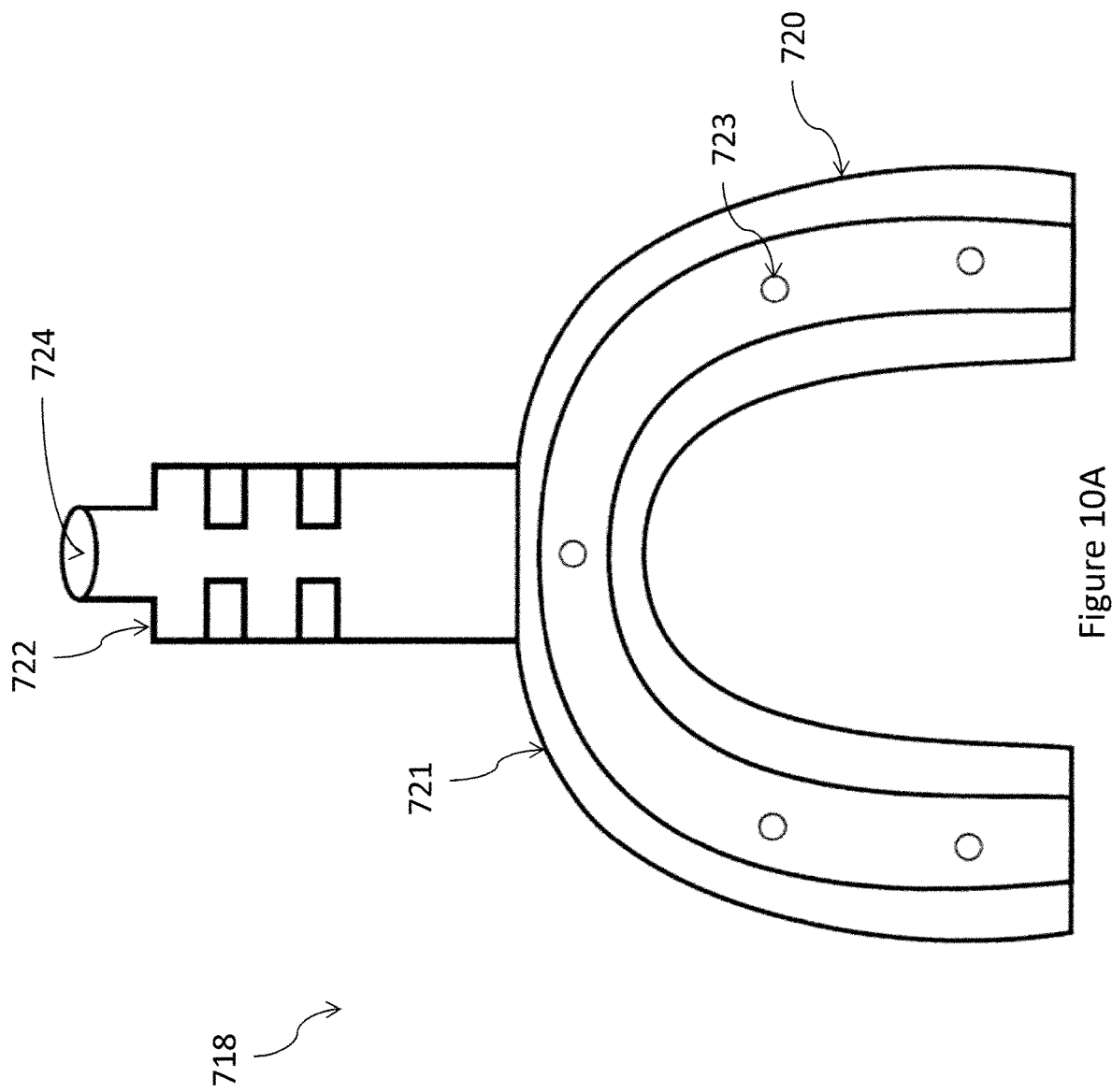
FIG. 10A is a top plan view of an eighth embodiment of an accessory device according to an aspect of the present invention.
Figure 10B:
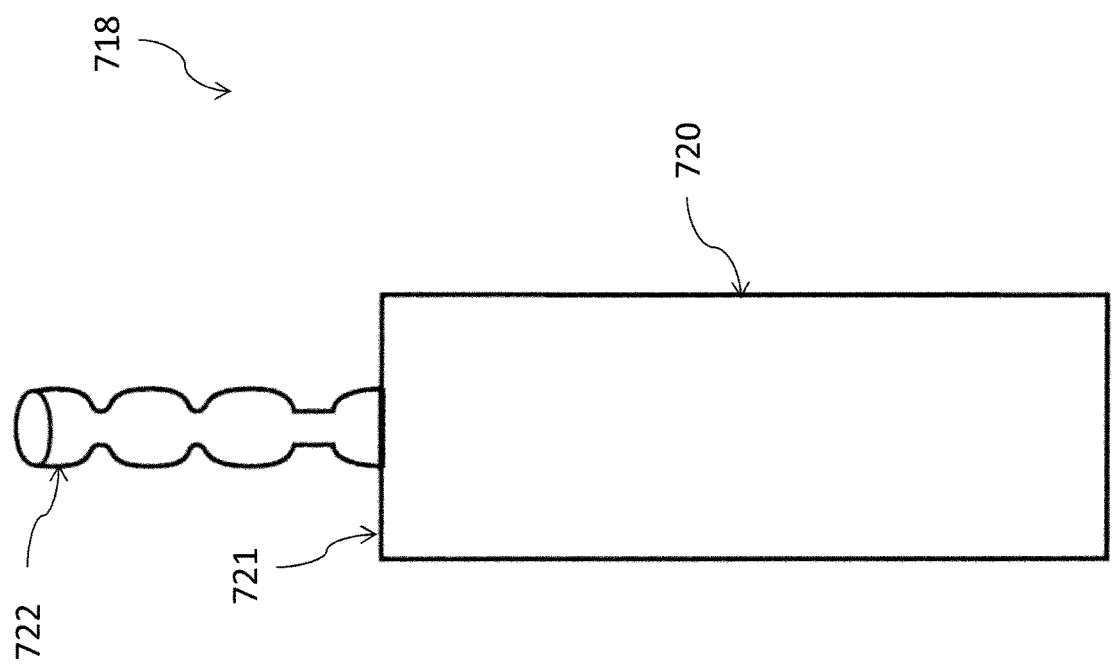
FIG. 10B is a side view of the embodiment of FIG. 10A.

In another embodiment of the present invention illustrated in FIGS. 10A and 10B, an accessory device 718 includes a patient fixation portion in the form of a mouthpiece 720 with an integrated palate vacuum outlet 724. The locking feature 722 has a configuration similar to the first embodiment of the present invention described above; however, the vacuum system can be adapted to any of the aforementioned configurations of the locking feature. It is often desirable to be able to make a custom impression of the upper palate and/or teeth of the patient. This can be particularly beneficial in edentulous patient cases (patients without teeth). A system which allows a vacuum to be pulled between the impression and the upper palate may be incorporated in the embodiments of the present invention. Such a system is described in U.S. Pat. No. 5,797,924, the contents of which are incorporated herein by reference. In the embodiment illustrated in FIG. 10A, air passages 723 are provided in the mouthpiece 720 of the accessory device 718, such that a vacuum can be drawn between the bite portion and the patient's upper palate. The air passages 723 are fluidly connected to a palate vacuum 724 outlet in the locking feature 722 such that air may pass through the LT thermoplastic material and out through the outlet 724. A vacuum tube (not shown) may be attached to the palate vacuum 724 outlet on the outside of the immobilization mask.

Figure 13:
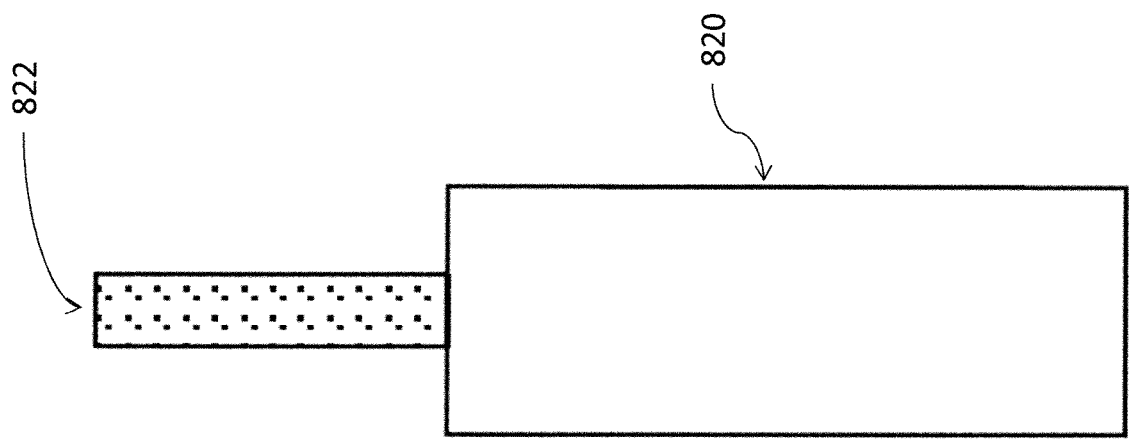
FIG. 13 is a side view of a ninth embodiment of an accessory device according to an aspect of the present invention.

In yet another embodiment of the present invention illustrated in FIG. 13, an accessory device 818 includes a locking feature 822 in the form of a post extending from the front surface 821 of a patient fixation portion in the form of a mouthpiece 820. The post may be coated with an adhesive substance that will adhere to the LT thermoplastic material. For example, a coating of poly-caprolactone (PCL) will allow the portion of the LT thermoplastic material in contact with the locking feature to stick adhesively to the accessory device. As would be understood by those of skill in the art, the combination of an adhesive with any of the aforementioned configurations for the locking feature or variations thereof would further facilitate fixation of the accessory device to the hardened LT thermoplastic material.

Figure 15A:
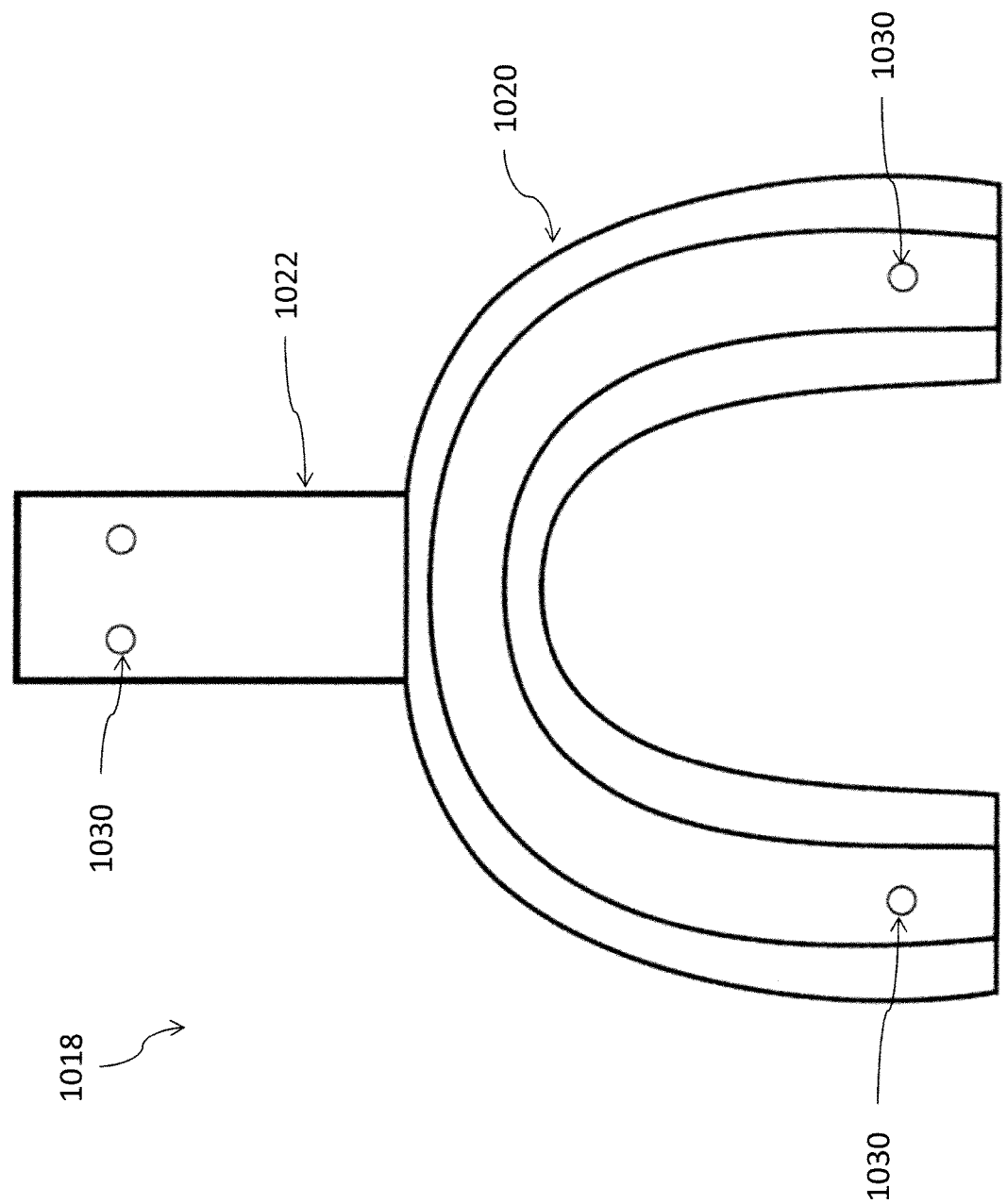
FIG. 15A is a top plan view of a ninth embodiment of an accessory device according to an aspect of the present invention.
Figure 15B:
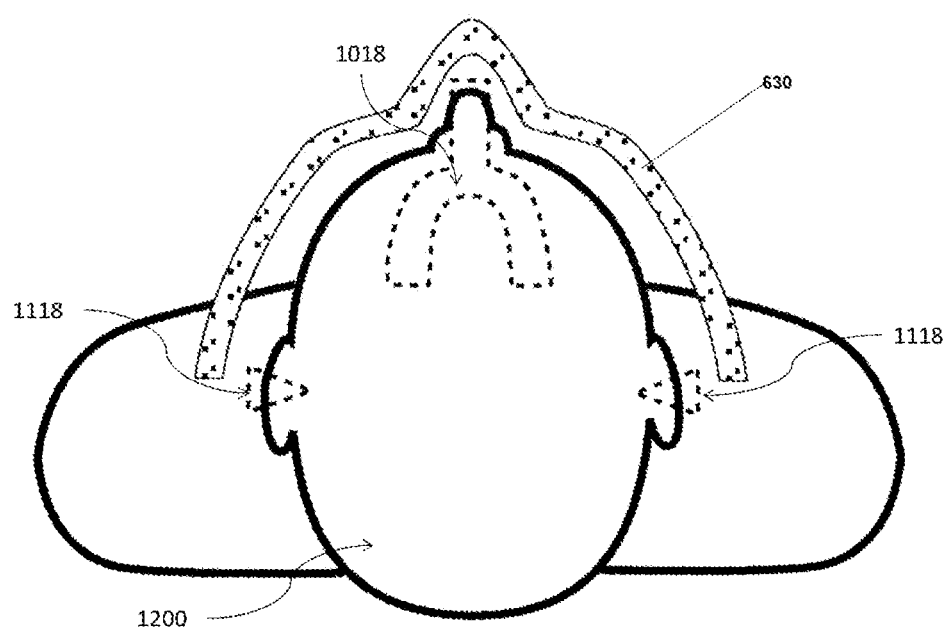
FIG. 15B is a front view of a patient in which a plurality of accessory device having been inserted, including the embodiment of FIG. 15A.

In yet another embodiment of the present invention illustrated in FIG. 15A, an accessory device 1018 may optionally include fiducial markers 1030 in various locations, such as the lock portion 1022 or the patient fixation portion 1020 of the accessory device 1018. Fiducial markers are design to be tracked through modalities such as x-ray, MRI, RF tracking, etc. They provide a surrogate location for the tumor and are generally tracked back to their position at the time of simulation for treatment. These fiducial markers include, but are not limited to, gold seed markers, Calypso Beacons, other x-ray markers, MRI markers, etc. as known to one skilled in the art. The markers may be embedded in the accessory device to enable the identification of the location as well as orientation of the accessory device. The use of at least three markers may also enable three-dimensional triangulation of the position of the tumor. For example, a plurality of x-ray opaque markers, preferably three or four, may be associated with an accessory device configured for insertion in the mouth and each ear to allow interpolation of the location of a tumor in the cranium. These markers may be coupled to the accessory devices, the thermoplastic material, or any other feature of the systems according to the present invention. For example referring to FIG. 15B, a plurality of accessory devices (1018, 1118) are illustrated in the installed condition and comprise one accessory device 1018, having a lock portion 1019 for oral insertion and two accessory devices 1118 each having a lock portion 1119 for insertion in each ear of the patient 1200. Each of the accessory devices may include at least one fiducial marker to identify the relative locations of the accessory devices, thereby triangulating the position of the patient's head. FIG. 15B also shows a base plate (1120) that the low temperature sheet (1122) may be attached to, such that the low temperature thermoplastic sheet 630 is proximal to a patient.

Accessory devices of this invention may be produced by any means known to those of skill in the art. For example, the accessory devices may be manufactured through any number of 3D printing methods. 3D printing provides a way of enabling the production of a patient specific accessory devices. Digital patient anatomy data may be used to develop the custom geometry for a patient fixation portion of the accessory devices and may be acquired through a number of methods, including but not limited to optical scanning, laser scanning, x-ray data, CT data, and MRI data. This data is often provided in the form of a DICOM data set and may be stored for multiple patients in a database of patient specific accessory devices. The data may be provided in any number of formats including, but not limited to, standard CAD formats. The patient specific portion of the accessory device may be designed using the data from the scanned patient. The design of the locking feature and patient specific portion could then be coupled using software. Additional desired features could then be added or designed using the software. For example, in the case of a mouthpiece, a custom tongue or epiglottis blocking feature may be desirable. The channels for a vacuum enhanced bite block may also be included in this way. Once the digital accessory device design has been completed, it would then be printed by the 3D printer.

Although the description of this invention has concentrated on the application to radiation therapy, it is to be understood that the invention also applies for applications such as neurosurgery, occupational therapy, orthotic devices, plastic surgery, etc. where enhanced positioning or immobilization are required.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An accessory device configured to position a patient relative to an immobilization device including a low temperature thermoplastic sheet, the accessory device comprising:
    a patient fixation portion configured for fixation on or insertion into the patient during use; and
    a lock portion extending distally from the patient fixation portion generally along a lock portion axis;
    wherein the accessory device is configured to be engaged by and to contact a proximal surface of the low temperature thermoplastic sheet by forming the proximal surface of the low temperature thermoplastic sheet around the lock portion of the accessory device, such that the proximal surface of the low temperature thermoplastic sheet conforms to the lock portion and when engaged prevents unintended separation of the accessory device from the low temperature thermoplastic sheet during use;
    wherein when engaged, the lock portion does not penetrate the low temperature thermoplastic sheet from the proximal surface of the low temperature thermoplastic sheet to a distal surface of the low temperature thermoplastic sheet; and
    wherein the proximal surface of the low temperature thermoplastic sheet is positionable proximal the patient and the distal surface of the low temperature thermoplastic sheet is opposite from the proximal surface.

2. The accessory device according to claim 1, wherein the lock portion includes at least one projection extending transverse to the lock portion axis.

3. The accessory device according to claim 2, wherein the at least one projection comprises a configuration selected from the group consisting of a T-shape, a Y-shape, a X-shape, a fan shape, a bow-tie shape, a ring shape, an oblong shape, a rhombus shape, a rectangle, and a circle.

4. The accessory device according to claim 2, wherein the at least one projection extends in a transverse direction.

5. The accessory device according to claim 2, wherein the at least one projection extends in a superior/inferior direction.

6. The accessory device according to claim 1, wherein the lock portion comprises an engaging end portion extending from the patient fixation portion, the engaging end portion having a variable cross-sectional area along and orthogonal to the lock portion axis.

7. The accessory device according to claim 6, wherein the lock portion further comprises a stem portion extending from the patient fixation portion to the engaging end portion.

8. The accessory device according to claim 1, wherein the patient fixation portion comprises a mouthpiece having a U-shaped configuration.

9. The accessory device according to claim 8, wherein the mouthpiece comprises a palate vacuum outlet.

10. The accessory device according to claim 1, wherein the lock portion defines at least one ridge.

11. The accessory device according to claim 1, wherein the lock portion defines at least one notch.

12. The accessory device according to claim 1, wherein the lock portion defines at least one hole.

13. The accessory device according to claim 1 further comprising an adhesive coating applied to a surface of the engaging end portion.

14. The accessory device according to claim 1 comprising a plurality of lock portions extending from the patient fixation portion.

15. The accessory device according to claim 1, wherein the accessory device is a single piece design.

16. An immobilization system configured to immobilize a patient, the immobilization system comprising:
    an immobilization device including a low temperature thermoplastic sheet; and
    an accessory device configured to position at least a portion of a body of the patient relative to the immobilization device, the accessory device including
    a patient fixation portion configured for fixation on or insertion into the patient during use; and
    a lock portion extending distally from the patient fixation portion generally along a lock portion axis;
    wherein the accessory device is configured to engage and to contact a proximal surface of the low temperature thermoplastic sheet with the proximal surface of the low temperature thermoplastic sheet formed around the lock portion of the accessory device, and when engaged prevents unintended separation of the accessory device from the low temperature thermoplastic sheet during use;
    wherein when engaged condition, the lock portion of the accessory device does not penetrate the low temperature thermoplastic sheet from the proximal surface of the low temperature thermoplastic sheet to a distal surface of the low temperature thermoplastic sheet; and
    wherein the proximal surface of the low temperature thermoplastic sheet is positionable proximal the patient and the distal surface of the low temperature thermoplastic sheet is opposite from the proximal surface.

17. The immobilization system according to claim 16 further comprising a fiducial marker embedded in the accessory device.

18. The immobilization system according to claim 17 comprising a plurality of fiducial markers, wherein the fiducial markers are configured to enable triangulation of the position of at least a portion of the body of the patient.

19. The immobilization system according to claim 16 further comprising a plurality of accessory devices.

20. A method of forming an immobilization system configured to immobilize at least a portion of a body of a patient, the method comprising the steps of:
    attaching or inserting a patient fixation portion of an accessory device on or in the patient;
    positioning a proximal surface of a low temperature thermoplastic sheet of an immobilization device to contact a lock portion of an accessory device extending distally from the patient fixation portion of the accessory device;
    forming the low temperature thermoplastic sheet of the immobilization device about the portion of the body of the patient; and
    forming the proximal surface of the low temperature thermoplastic sheet around the lock portion of the accessory device, such that unintended separation of the accessory device from the low temperature thermoplastic sheet is prevented; and
    wherein the lock portion of the accessory device does not penetrate the low temperature thermoplastic sheet from the proximal surface of the low temperature thermoplastic sheet to a distal surface of the low temperature thermoplastic sheet; and
    wherein the proximal surface of the low temperature thermoplastic sheet is positionable proximal the patient and the distal surface of the low temperature thermoplastic sheet is opposite from the proximal surface.

21. The method of claim 20, wherein the portion of the body of the patient includes the cranial region.

22. The method of claim 20 further comprising attaching the low temperature thermoplastic sheet to a base plate.

23. A method of making an accessory device configured to position a patient relative to an immobilization device including a low temperature thermoplastic sheet, the method comprising:

scanning an anatomy of a patient and acquiring geometry data of the anatomy of the patient, selecting a configuration of a locking feature, and forming an accessory device comprising the locking feature coupled to an anatomical portion having a configuration corresponding to the anatomy of the patient, wherein the locking feature is configured to prevent unintended separation of the accessory device from the low temperature thermoplastic sheet during use;

wherein the accessory device is configured to be engaged by a proximal surface of the low temperature thermoplastic sheet by forming the proximal surface of the low temperature thermoplastic sheet around the lock portion of the accessory device, such that the proximal surface conforms to the lock portion and the engagement prevents the unintended separation of the accessory device from the low temperature thermoplastic sheet during use;

wherein the locking feature of the accessory device does not penetrate the low temperature thermoplastic sheet from the proximal surface of the low temperature thermoplastic sheet to a distal surface of the low temperature thermoplastic sheet in the engaged condition; and wherein the proximal surface of the low temperature thermoplastic sheet is positionable proximal the patient and the distal surface of the low temperature thermoplastic sheet is opposite from the proximal surface.

24. The method of claim 23, wherein the forming step is performed using a 3D printer.

25. The method of claim 23, wherein the accessory device is a single piece design.

* * * * *